United States Patent
Halfaker

(10) Patent No.: US 10,299,962 B1
(45) Date of Patent: *May 28, 2019

(54) NOISE REDUCTION EARMUFFS SYSTEM AND METHOD

(71) Applicant: Alvin J. Halfaker, Grand Rapids, MN (US)

(72) Inventor: Alvin J. Halfaker, Grand Rapids, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/186,734

(22) Filed: Nov. 12, 2018

Related U.S. Application Data

(63) Continuation of application No. 16/004,074, filed on Jun. 8, 2018, now Pat. No. 10,149,786.

(51) Int. Cl.
| | |
|---|---|
| *A61F 11/14* | (2006.01) |
| *A42B 3/16* | (2006.01) |
| *A42B 3/30* | (2006.01) |
| *G10K 11/178* | (2006.01) |

(52) U.S. Cl.
CPC .............. *A61F 11/14* (2013.01); *A42B 3/163* (2013.01); *A42B 3/166* (2013.01); *A42B 3/303* (2013.01); *G10K 11/178* (2013.01); *A61F 2011/145* (2013.01)

(58) Field of Classification Search
CPC .... A61F 11/14; A61F 2011/145; A42B 3/166; A42B 3/303; A42B 3/163; G10K 11/178
USPC ........... 381/71, 77, 71.6, 94.7, 122; 704/226
See application file for complete search history.

(56) References Cited

U.S. PATENT DOCUMENTS

| | | | |
|---|---|---|---|
| 2012/0183160 A1* | 7/2012 | Abe | G10K 11/178 381/123 |
| 2016/0365082 A1* | 12/2016 | Poulsen | H04R 5/033 |
| 2017/0301339 A1* | 10/2017 | Hui | G08B 3/00 |

* cited by examiner

*Primary Examiner* — Melur Ramakrishnaiah
(74) *Attorney, Agent, or Firm* — Uradnik Law Firm PC

(57) ABSTRACT

An earmuffs system for noise reduction including an external microphone used in combination with active noise cancellation technology for the reduction of wind or other noises typically experienced while riding a vehicle such as a motorcycle, snow machine or ATV, the earmuffs system including a first earmuff including a first speaker and a first microphone therein; a second earmuff electrically coupled to the first ear muff, the second ear muff including a second speaker and a second microphone therein; noise cancellation circuitry for receiving first sounds from the first microphone and the second microphone and processing the first sounds by in part canceling the first sounds to form a first sound output that is provided from the first speaker and the second speaker; and a third microphone placed external to the first earmuff and to the second earmuff, the third microphone supplying second sounds for the first speaker and the second speaker to output as a second sound output without the second sounds undergoing noise cancellation processing.

27 Claims, 5 Drawing Sheets

NOISE REDUCTION EARMUFFS SYSTEM AND METHOD

RELATED APPLICATIONS

This application is a continuation of, and relates and claims priority to, U.S. patent application Ser. No. 16/004,074, filed on Jun. 8, 2018, now U.S. Pat. No. 10,149,786 issued on Dec. 11, 2018.

FIELD OF THE DISCLOSURE

The invention relates generally to an earmuffs system and method, and more particularly, to an earmuffs system including an external microphone used in combination with active noise cancellation technology for the reduction of wind and other noises typically experienced while riding a vehicle such as a motorcycle, snow machine, ATV, etc.

BACKGROUND

Users of vehicles such as motorcycles, snow machines, ATVs, etc., often wear helmets for protection. For convenience, reference is made herein primarily to motorcycle riders and helmets only; however, the invention is not so limited.

Even with helmet use, a problem remains in that motorcycle riders experience excessive wind noise. Wind noise occurs when wind hits a solid surface. The surface vibrates, and the vibrations are picked up by the eardrums as noise. The ears can safely endure noise levels of 0 dB to 80 dB. However, the wind noise level in most motorcycle helmets can average between 95 dB and 105 dB or more, depending upon the speed of travel of the motorcycle.

Exposure to wind noise can lead to permanent hearing loss. Wind noise also tends to fatigue a rider. Wind noise also interferes with communications systems used by riders.

Numerous attempts have been made to filter or reduce wind noise for motorcycle riders. Aerodynamic helmets that allow the wind to pass more easily over them have been used. The use of earplugs also has been tried. However, filtering wind noise tends to muffle out important sounds like communications, sirens from emergency vehicles, engine noises, vehicle horns, etc.

Thus, there remains a need for a system and method to provide improved wind noise reduction without the drawbacks of prior approaches to the problem.

SUMMARY

The present disclosure provides a noise reduction system and method for motorcycle riders that includes a helmet having an external microphone used in combination with active noise cancelling technology. The external microphone provides the rider with the sounds of sirens, engines, horns, and the like, which otherwise would be muffled by the active noise cancellation system.

By way of example only, an earmuffs system for a helmet or headphones system includes: a first ear muff including a first speaker and a first microphone therein; a second earmuff electrically coupled to the first ear muff, the second ear muff including a second speaker and a second microphone therein; noise cancellation circuitry disposed within the first ear muff, the noise cancellation circuitry receiving first sounds from the first microphone and the second microphone and processing the first sounds by in part canceling the first sounds to form a sound output that is provided from the first speaker and the second speaker; and a third microphone placed external to the helmet or headphones system, the third microphone supplying second sounds for the first speaker and the second speaker to output without the second sounds undergoing noise cancellation processing.

Other benefits and advantages of the present disclosure will be appreciated from the following detailed description.

DETAILED DESCRIPTION

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to earmuffs use; etc. Such aspects related to this disclosure do not depart from the invention, and it is therefore intended that the invention not be limited by the certain aspects set forth of the events and circumstances related to this disclosure.

Figure 1:
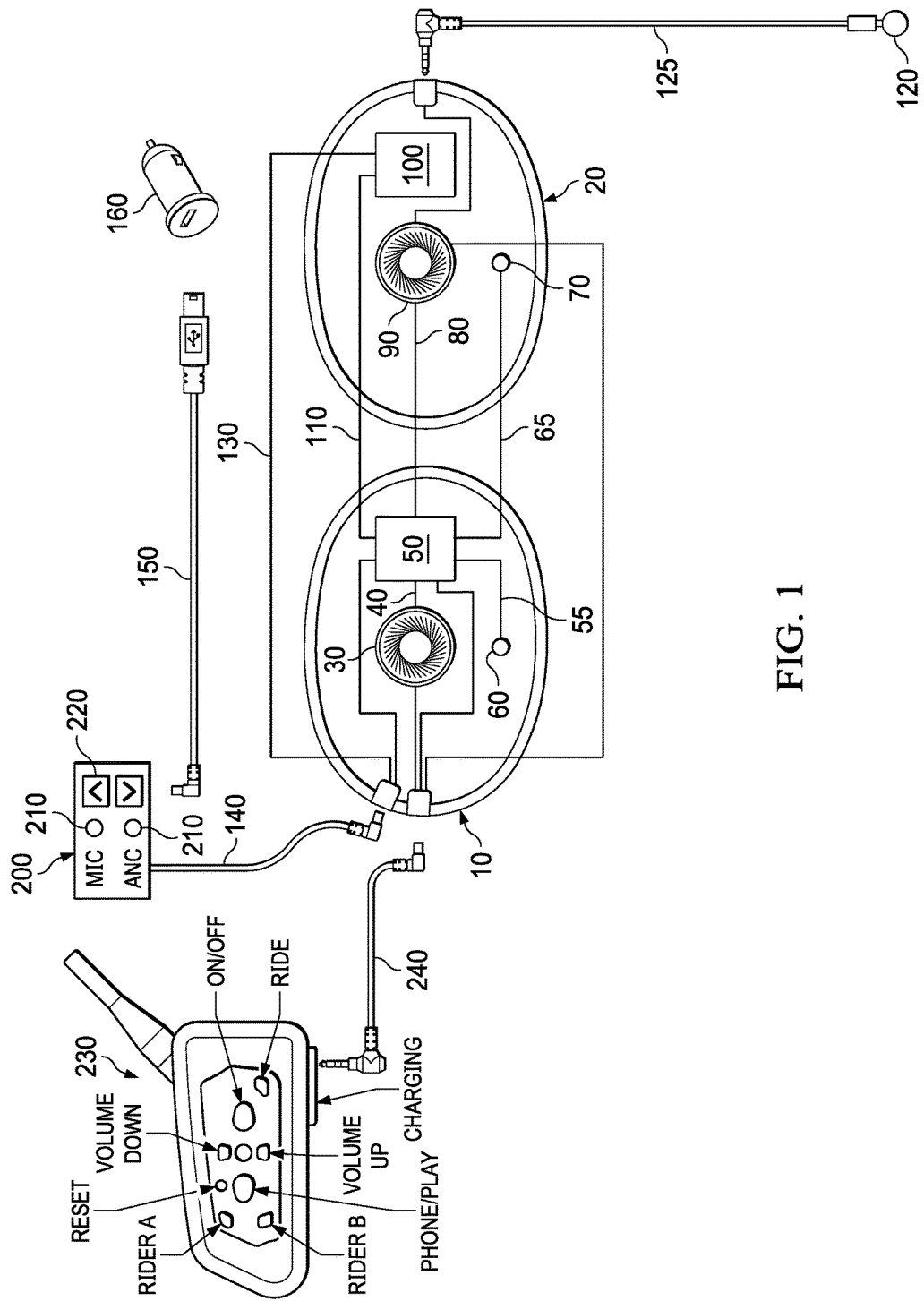
FIG. 1 is a view in partial schematic form of an exemplary embodiment of a noise reduction earmuffs system.
Figure 2A:
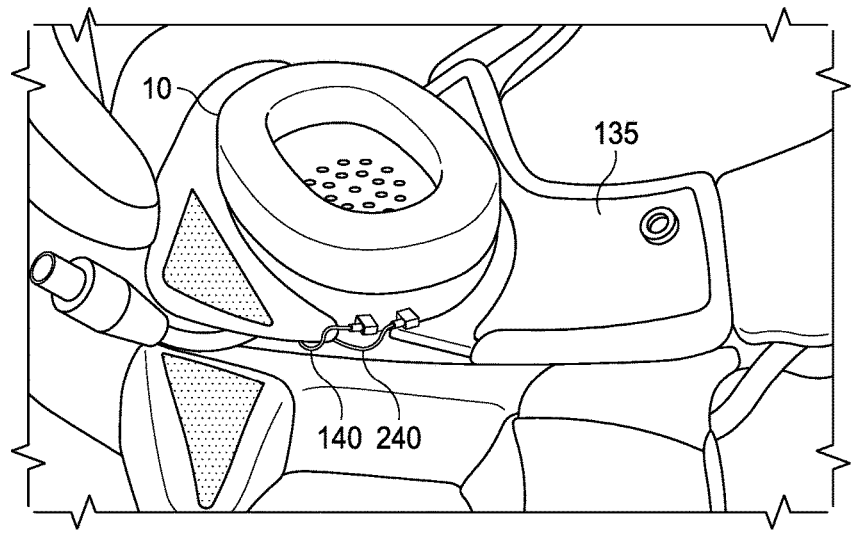
FIG. 2A is a perspective view of an earmuff and padding on a first side of a helmet including the exemplary embodiment of a earmuffs system shown in FIG. 1.
Figure 2B:
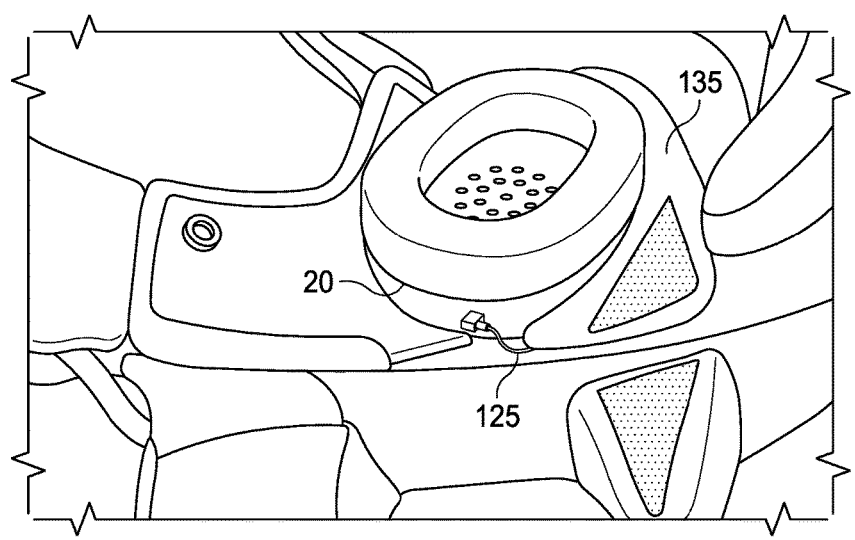
FIG. 2B is a perspective view of an earmuff and padding on a second side of a helmet including the exemplary embodiment of an earmuffs system shown in FIG. 1.

Turning now to the drawings, FIG. 1 shows an exemplary earmuffs system suited for wind and other noise reduction. The system includes a first earmuff 10 and a second earmuff 20. The earmuffs 10, 20 may be adapted to fit over the ears of a system user, or may be otherwise placed on the ear. Earmuff 10 includes a speaker 30 electrically coupled via line 40 to an active noise cancellation circuit board 50. Microphone 60 in earmuff 10, and microphone 70 in earmuff 20, provide a first sound input to the circuit board 50 via lines 55, 65 respectively. The circuit board 50 processes the ambient sounds received from microphones 60, 70 (i.e., the first sound), and provides a second sound that is specifically designed to cancel in whole or in part the first sound. The second sound may be 180 degrees out of phase with the first sound. The circuit board 50 is electrically coupled to speaker 30 in earmuff 10 and speaker 90 in earmuff 20 via lines 40, 80 respectively.

Although reference is made herein to active noise cancellation technology, such technology might also be referred to as active noise control or active noise reduction. Each of these approaches to noise cancellation may be used in connection with the present invention.

Power to the active noise cancellation circuit board 50 may be provided from battery 100. As shown, battery 100 is disposed in earmuff 20, and circuit board 50 is disposed in earmuff 10, with a line 110 connecting the two. However, the placement of the battery 100 and circuit board 50 ultimately will depend upon the circumstances involved in a particular application.

An external microphone 120 may be provided that is electrically coupled to ear muffs 10, 20 via line 125. The external microphone 120 may be situated at the center, rear of the helmet 130. See FIG. 3. The external microphone 120 provides sounds to the rider that would otherwise be overly muffled by the noise cancellation system. Sounds that the external microphone 120 may provide include an acceptable level of engine noise; sirens of emergency vehicles; car horns or other warning signals; etc. The sounds provided by external microphone 120 may be processed by circuit board 50; however, the sounds will not be overly cancelled or reduced as a result of such processing, so that the sounds may be heard by the rider. The earmuffs 10, 20 may be disposed within or surrounded by the padding 135 of helmet 130.

The battery 100 may be charged via lines 130, 140, 150 using a 12 Volt adapter 160 that plugs into the motorcycle or other vehicle. A control unit 200 may be positioned on the exterior of the helmet 130. The control unit 200 may include lights 210 to indicate that one or both of the external microphone (MIC) and active noise cancellation (ANC) components are operational. The control unit 200 also may include a volume control 220 that may adjust upward or downward the sound heard from speakers 30, 90.

Figure 3:
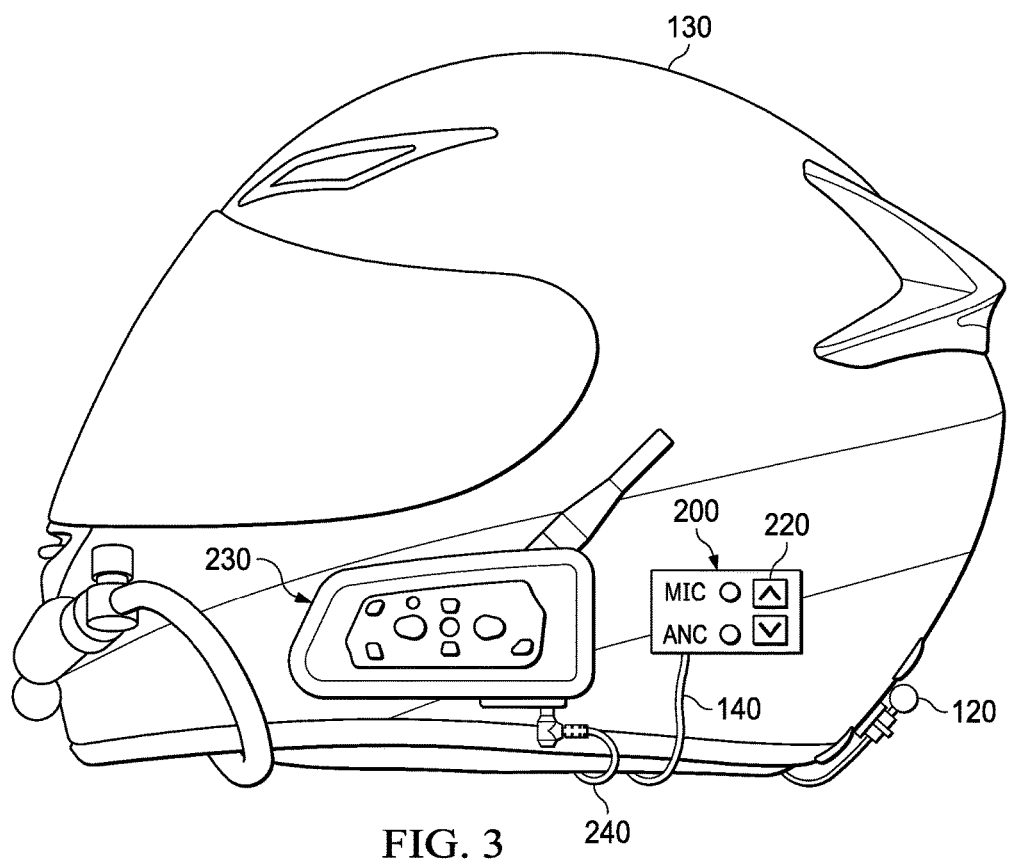
FIG. 3 is a side view of a helmet including the exemplary embodiment of an earmuffs system shown in FIG. 1, which is equipped with a communications system and system control board.

The earmuffs system of the present invention also may be used in combination with a commercially available intercom system that allows rider to rider intercommunications. An exemplary intercom controller 230 is shown in FIGS. 1, 3, and 4A, and is connected to the earmuff 10 via line 240.

Figure 4A:
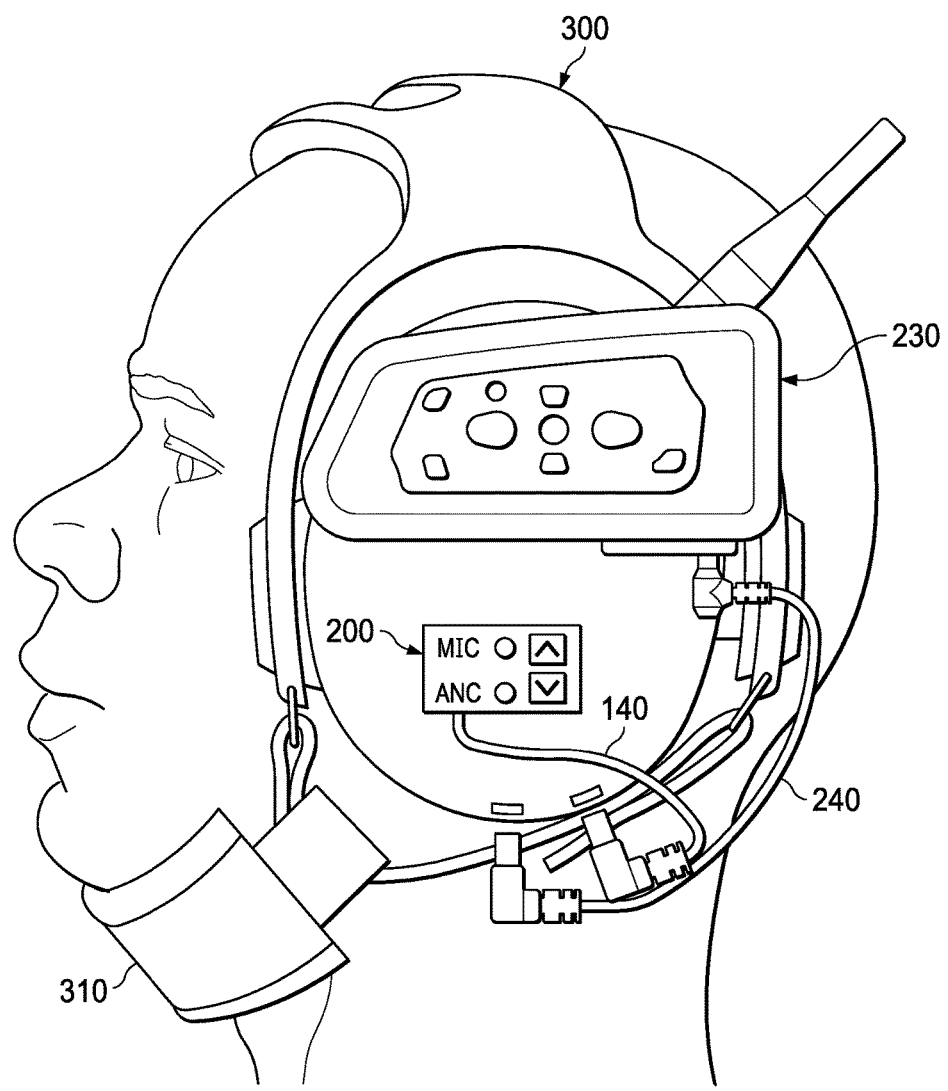
FIG. 4A is a first side view of an exemplary embodiment of an earmuffs system shown in FIG. 1, embodied in a headphones system.
Figure 4B:
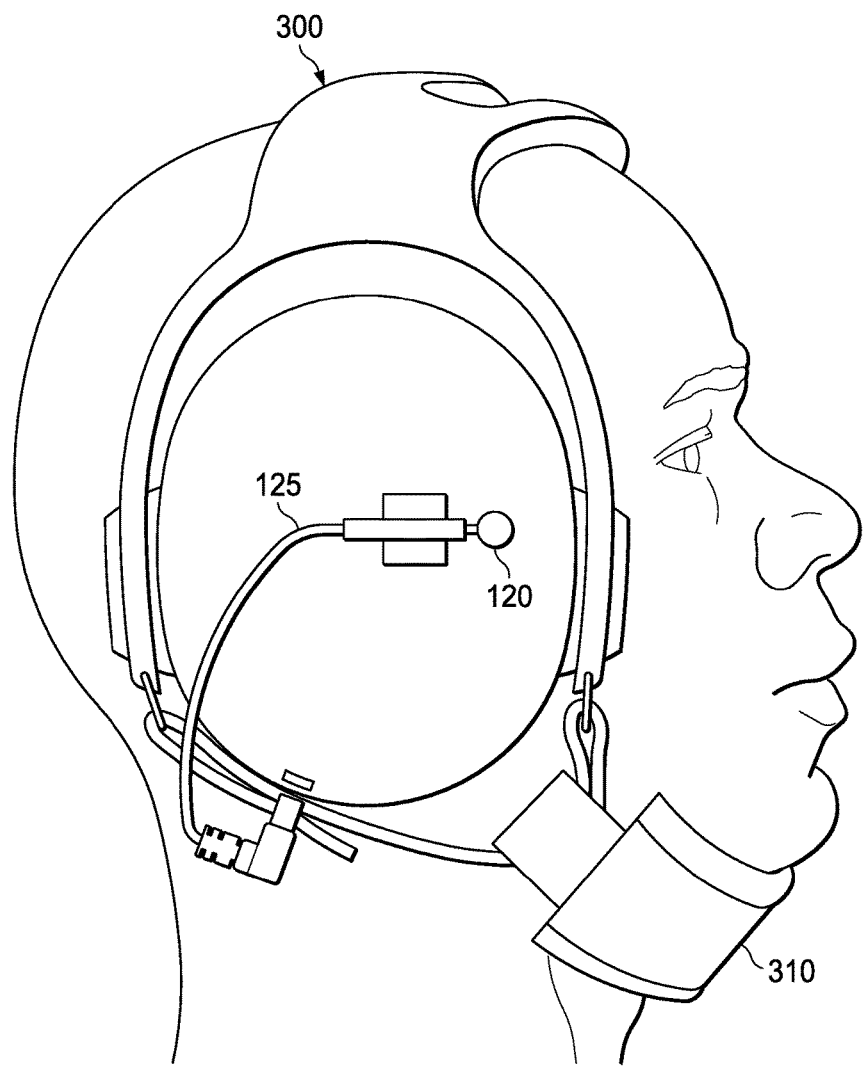
FIG. 4B is a second side view of an exemplary embodiment of an earmuffs system shown in FIG. 1, embodied in a headphones system.

Another embodiment of the invention is shown in FIGS. 4A and 4B. Here, the earmuffs with active noise cancellation technology are embodied in a headphones system. The headphones system includes a frame 300 upon which the earmuffs may be mounted. A chin strap 310 may be used to hold the frame 300 in place so that the earmuffs are positioned over a rider's ears. On one side of the headphones system the control unit 200 and the intercom controller 230 may be positioned for ease of access by a rider. On the opposite side of the headphones system the external microphone 120 may be positioned. In one embodiment, the external microphone may be positioned proximate a shield used to reduce wind and other noise effects on the microphone 120. In another embodiment, with or without a shield, the external microphone 120 may be adapted with a cover for the reduction of wind and other noises. One example of such a cover may be the use of foam, either alone or in conjunction with the use of fur.

An exemplary method in accordance with the present invention may involve the steps of: providing to an individual a first sound output comprising a first ambient sound that is at least partially cancelled by a second sound that is out of phase with the first ambient sound; and a second sound output that is provided without noise cancellation or noise reduction processing; wherein the first ambient sound is supplied by one or more microphones disposed proximate one or more of the individual's ears in one or more over-the-ear earmuffs, and wherein the second sound output is supplied from a microphone positioned external to the earmuffs. In one exemplary embodiment, the first ambient sound is detected within a helmet or a headphones system, and the second sound output is supplied from a microphone external to the helmet or the headphones system. In another exemplary embodiment, an individual is provided a helmet or a headphones system that provides the individual with a first sound output that has undergone noise cancellation processing and a second sound output that has not undergone noise cancellation processing, wherein the first sound output is supplied by one or more microphones internal to the helmet or headphones system, and the second sound output is supplied by one or more microphones external to the helmet or headphones system.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

What is claimed is:

1. An earmuffs system for a helmet including:
    a first ear muff including a first speaker and a first microphone therein;
    a second earmuff electrically coupled to the first ear muff, the second ear muff including a second speaker and a second microphone therein;
    noise cancellation circuitry disposed within the helmet, the noise cancellation circuitry receiving first sounds from the first microphone and the second microphone and processing the first sounds by in part canceling the first sounds to form a first sound output that is provided from the first speaker and the second speaker; and a third microphone placed external to the helmet, the third microphone supplying second sounds for the first speaker and the second speaker to output as a second sound output.

2. The earmuffs system of claim 1 including a control unit electrically coupled to the noise cancellation circuitry for adjusting the volume of the first sound output or the second sound output.

3. The earmuffs system of claim 1 including a control unit electrically coupled to the first speaker and the second speaker to adjust a sound volume from the first speaker or the second speaker.

4. The earmuffs system of claim 1, wherein at least one of the first speaker and the second speaker provide the first sound output and the second sound output simultaneously.

5. The earmuffs system of claim 1, wherein the first speaker and the second speaker are electrically coupled to a rider-to-rider intercommunication system.

6. The earmuffs system of claim 1, wherein the second earmuff includes a battery electrically coupled to the noise cancellation circuitry.

7. The earmuffs system of claim 6, wherein the battery is rechargeable via an adaptor for use with a twelve-volt receptacle in a vehicle.

8. An earmuffs system including:
a first earmuff including a first speaker and a first microphone therein;
a second earmuff electrically coupled to the first ear muff, the second ear muff including a second speaker and a second microphone therein;
noise cancellation circuitry for receiving first sounds from the first microphone and the second microphone and processing the first sounds by in part canceling the first sounds to form a first sound output that is provided from the first speaker and the second speaker; and
a third microphone placed external to the first earmuff and to the second earmuff, the third microphone supplying second sounds for the first speaker and the second speaker to output as a second sound output.

9. The earmuffs system of claim 8, wherein the first sound output and the second sound output are provided simultaneously by one or more of the first speaker and the second speaker.

10. The earmuffs system of claim 8 embodied in a helmet.

11. The earmuffs system of claim 8 embodied in a headphones system.

12. The earmuffs system of claim 8 including a control unit for adjusting the volume of sound provided by the first speaker or the second speaker.

13. The earmuffs system of claim 8 including a rider-to-rider intercommunication system electrically coupled to at least one of the first earmuff and the second earmuff.

14. An earmuffs system for a helmet including:
a first ear muff including a first speaker therein;
a second ear muff electrically coupled to the first ear muff, the second ear muff including a second speaker therein;
a first microphone and a second microphone within the helmet;
noise cancellation circuitry disposed within the first ear muff, the noise cancellation circuitry receiving first sounds from the first microphone and the second microphone and processing the first sounds by in part canceling the first sounds to form a first sound output that is provided from the first speaker and the second speaker; and a third microphone placed external to the helmet, the third microphone supplying second sounds for the first speaker and the second speaker to output as a second sound output.

15. The earmuffs system of claim 14 including a control unit electrically coupled to the noise cancellation circuitry for adjusting the volume of the first sound output or the second sound output.

16. The earmuffs system of claim 14 including a control unit electrically coupled to the first speaker and the second speaker to adjust a sound volume from the first speaker or the second speaker.

17. The earmuffs system of claim 14, wherein at least one of the first speaker and the second speaker provide the first sound output and the second sound output simultaneously.

18. The earmuffs system of claim 14, wherein the first speaker and the second speaker are electrically coupled to a rider-to-rider intercommunication system.

19. The earmuffs system of claim 14, wherein the second earmuff includes a battery electrically coupled to the noise cancellation circuitry.

20. The earmuffs system of claim 19, wherein the battery is rechargeable via an adaptor for use with a twelve-volt receptacle in a vehicle.

21. An earmuffs system for a helmet including:
a first ear muff including a first speaker therein;
a second earmuff electrically coupled to the first ear muff, the second ear muff including a second speaker therein;
a first microphone and a second microphone within the helmet;
noise cancellation circuitry disposed within the helmet, the noise cancellation circuitry receiving first sounds from the first microphone and the second microphone and processing the first sounds by in part canceling the first sounds to form a first sound output that is provided from the first speaker and the second speaker; and
a third microphone placed external to the helmet, the third microphone supplying second sounds for the first speaker and the second speaker to output as a second sound output without the second sounds undergoing noise cancellation processing.

22. The earmuffs system of claim 21 including a control unit electrically coupled to the noise cancellation circuitry for adjusting the volume of the first sound output or the second sound output.

23. The earmuffs system of claim 21 including a control unit electrically coupled to the first speaker and the second speaker to adjust a sound volume from the first speaker or the second speaker.

24. The earmuffs system of claim 21, wherein at least one of the first speaker and the second speaker provide the first sound output and the second sound output simultaneously.

25. The earmuffs system of claim 21, wherein the first speaker and the second speaker are electrically coupled to a rider-to-rider intercommunication system.

26. The earmuffs system of claim 21, wherein the second earmuff includes a battery electrically coupled to the noise cancellation circuitry.

27. The earmuffs system of claim 26, wherein the battery is rechargeable via an adaptor for use with a twelve-volt receptacle in a vehicle.

* * * * *